Aug. 12, 1952 H. C. SWIM Plant Pat. 1,119
ROSE PLANT
Filed July 10, 1951 2 SHEETS--SHEET 1
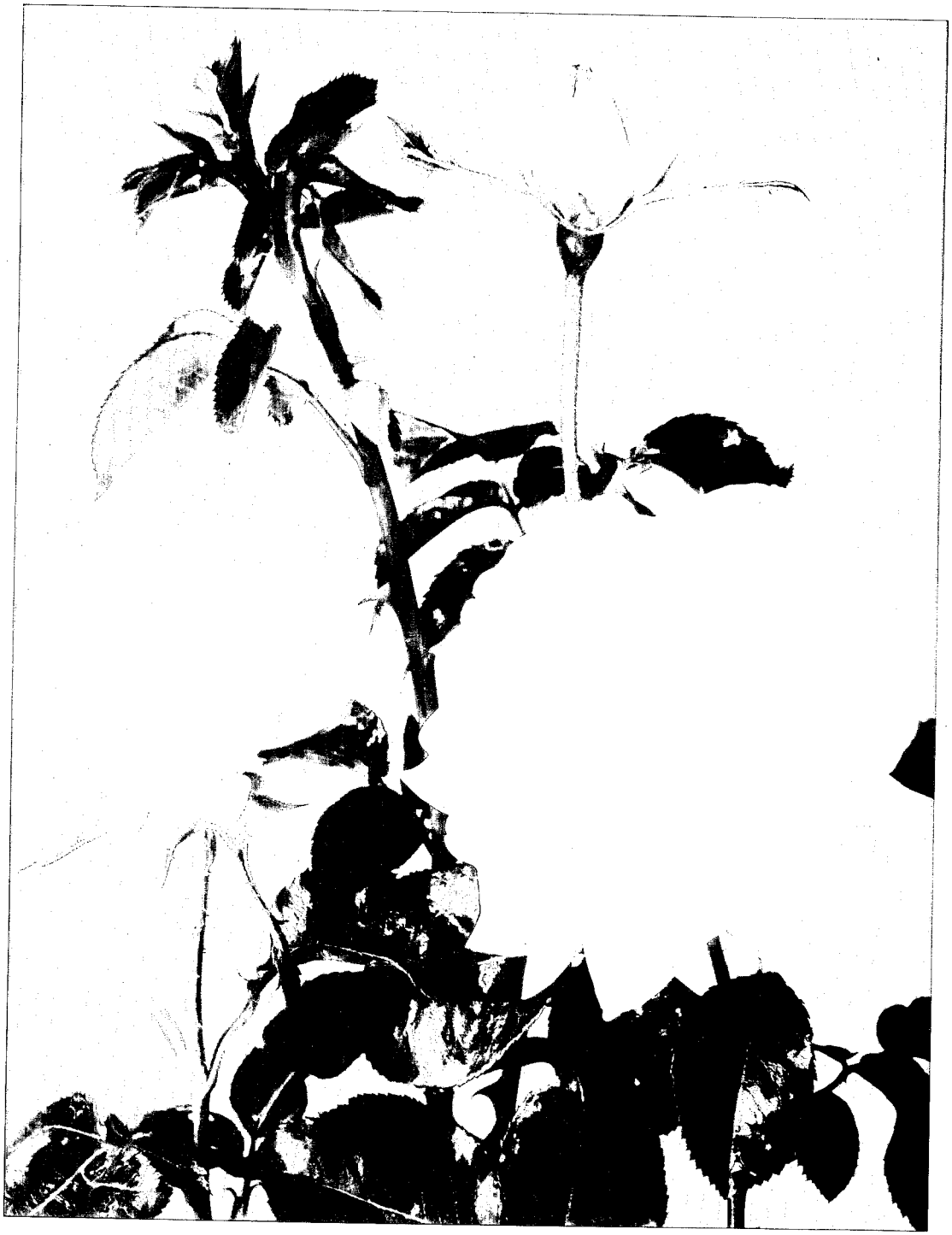
Inventor.
H. C. Swim
By: Robert Cobb
Attorneys ROSE PLANT
Filed July 10, 1951 2 SHEETS--SHEET 2
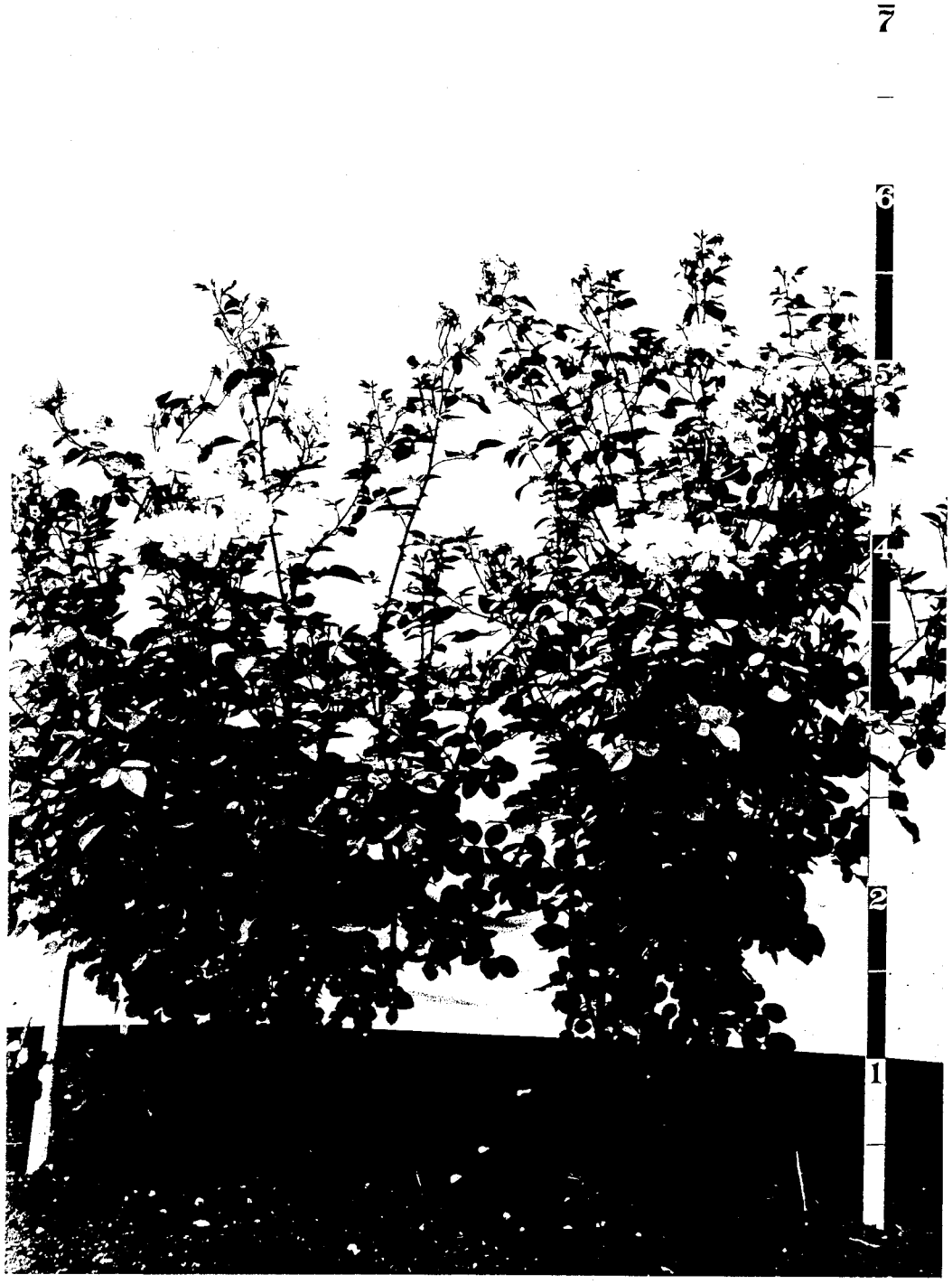
Inventor.
H. C. Swim
By: Robert Cobb
Attorneys.

Patented Aug. 12, 1952 Plant Pat. 1,119

UNITED STATES PATENT OFFICE 1,119

ROSE PLANT

Herbert C. Swim, Ontario, Calif., assignor to Armstrong Nurseries, Inc., Ontario, Calif., a corporation of California Application July 10, 1951, Serial No. 235,991

1 Claim. (Cl. 47—61)

The present invention relates to a new and distinct variety of rose plant of the hybrid tea class, resulting from crossing the variety "Golden Rapture" (unpatented) with an unnamed and unpatented seedling of "Max Krause" (unpatented) × "Captain Thomas" (Plant Patent No. 393).

This new variety is dominantly characterized as to novelty by the following unique combination of distinctive features which distinguish it from its parents, as well as from all other varieties of its class:

(1) The very vigorous and upright habits of growth of the plant;

(2) The normal to abundant foliage of a dark shade of green, substantially as illustrated and hereinafter described in more detail, said foliage being relatively flat and substantially larger than that of most roses of the hybrid tea class;

(3) The intense yellow color of the buds and flowers which is difficult to illustrate, but which is substantially as described and illustrated herein. Although yellow pigment normally is quite fugitive in most rose varieties heretofore known in commerce, this new variety is very long-lasting and maintains its pronounced yellow tones in the flowers during their entire life;

(4) The notable lack of any other color shading in the flowers of this new variety, whereas most yellow roses are prone to show pronounced markings of pink or red on the outside of the buds.

In comparison with its seed parent "Golden Rapture," the new variety differs therefrom by its much more vigorous habit of growth, usually attaining a height at least twice as tall as the parent; the longer-lasting quality of the yellow color of the flowers, which is a marked improvement over that of "Golden Rapture"; the greater proportion of length to width of the flower buds than it is in the seed parent; and the much larger foliage than the foliage of this parent.

Compared with its pollen parent, the new variety attains a brilliant yellow color in the buds and flowers, whereas the buds and flowers of the parent are a pale shade of yellow; the foliage of the new variety tends to grow large and flat instead of the medium size foliage of this parent which is usually rolled downward at the margin; the flowers of the new variety are borne on stems of normal strength and only slightly longer than normal length, whereas the pollen parent bears its flowers on stems of exceptional length (4 to 6 feet) and which are always pendulous in habit; and the new variety is free in its habit of bloom, while the pollen parent usually fails to produce a satisfactory quantity of blooms.

Asexual reproduction of the new variety by budding at Ontario, California, shows that the foregoing characteristics and distinctions come true to form and are established and transmitted through succeeding propagations.

The accompanying drawings show specimen plants of the new variety which are illustrated in black and white as representative of their habits of growth, and the flowers and foliage are also shown separately, in color, in different stages of development, and on a somewhat enlarged scale.

The following is a detailed description of the new variety, with color terminology in accordance with Robert F. Wilson's Horticultural Colour Chart, except where indicated to be in accordance with Ridgway's Color Standards and Nomenclature:

Type: Tall; bush; outdoor; seedling; for cut flowers and for garden decoration.

Class: Hybrid tea.

Breeding: Seedling.

*Seed parent.*—"Golden Rapture."

*Pollen parent.*—An unnamed seedling of "Max Krause" × "Captain Thomas."

Propagation: Holds its distinguishing characteristics through succeeding propagations of budding.

*Flower*

Locality where grown and observed: Ontario, California.

Flowers borne: Sometimes singly, sometimes two to three or more to stem; in irregular rounded cluster; on normally medium to long stems.

Quantity of bloom: Free; outdoors.

Continuity: Nearly continuous during growing season.

Fragrance: Moderate; tea.

Bud:

*Peduncle.*—Average length, 1¾ inches to 3½ inches; average calipers; bending to erect; numerous gland-tipped cilia, and few hairs and a few very small prickles. Color—near Calliste Green, Plate VI (Ridgway) on shaded portions; shaded very lightly with Hydrangea Red, Plate XXVII (Ridgway) on unshaded portions.

*Before calyx breaks.*—Size—medium. Form—medium length; pointed; ovoid; usually with foliaceous appendages and gland-tipped cilia and glandular bloom on the surface of the bud; usually with foliaceous parts extending beyond the tip of the bud equal to ½ to ¾ or more of its length.

*As calyx breaks.*—Color—near Primrose Yellow, Plate 601/1, page 65.

*Sepals.*—Inner surface—with woolly tomentum; margins that are covered have tomentum; exposed margins have stipitate glands.

*As first petal opens.*—Size—average to large. Form—medium length to long; pointed to urn-shaped. Color—outside: near Lemon Yellow, Plate 4, page 4, sometimes with markings of Buttercup Yellow, Plate 5/1, page 5, where the sepals have crossed the petal as the calyx broke; inside: Aureolin Yellow, Plate 3, page 3, toward the pedal base, darkening gradually to Lemon Yellow, Plate 4, page 4, over most of pedal surface. Opening—opens up well. Is not retarded from opening by cold, hot, wet, or dry weather.

Bloom:

*Size.*—When fully open—average; 3 inches to 3½ inches.

*Petalage.*—Double; from 28 to 38 petals, plus 4 to 8 petaloids; arranged regularly. An occasional flower has many more petals but only occasionally.

*Form.*—Cupped at first; becoming open; margins of outer petals at first are curved or loosely rolled outward while the innermost petals have their margins cupped inward. Later at maturity, the outer petal margins become more tightly rolled outward while the innermost petals become variable, some margins being rolled loosely outward and others curved inward, giving a somewhat crumpled conformation to these innermost petals.

Petals:

*Texture.*—Medium to thick; moderately leathery; with inside shiny to velvety and outside satiny.

*Shape.*—Outside—broadly obovate. Intermediate—obovate; apex sometimes with one notch. Inside—crumpled and twisted irregular in form; if pressed out, they are obovate for the most part, usually with one notch in apex. Sometimes a few of these inner petals are actually intermediate between petals and petaloids, not stalked but with the lower portion on one side of the center not developed, adding to the twisted conformation of these inner petals. The mid-portion of the lower half of many of these deformed petals are often thickened, appearing as a filament within this portion of the petal.

This description of a newly opened flower was made from a rose grown outdoors in the month of September, at Ontario, California:

*Color.*—Outside petal—outside surface: between Aureolin, Plate 3/2, page 3, and Lemon Yellow, Plate 4/2, page 4; inside surface: between Aureolin, Plate 3/1, page 3, and Lemon Yellow, Plate 4/2, page 4. Intermediate petal—outside surface: between Aureolin, Plate 3/2, page 3, and Lemon Yellow, Plate 4/2, page 4; inside surface: near Aureolin, Plate 3/1, page 3. Inner petal—outside surface: between Aureolin, Plate 3/2, page 3, and Aureolin, Plate 3/1, page 3; inside surface: near Aureolin, Plate 3/1, page 3.

This description was made from a rose that was open for three days outdoors in the month of September, at Ontario, California:

*Color.*—Outside petal—outside surface: between Aureolin, Plate 3/1, page 3, and Aureolin, Plate 3/2, page 3, near the base, fading rapidly upward to become near Primrose Yellow, Plate 601/3, page 65, at the petal edges; inside surface: near Aureolin, Plate 3/1, page 3, at the base, fading rapidly upward to become near Primrose Yellow, Plate 601/3, page 65, in the upper one-half of the petal. Inside petal—outside surface: near Empire Yellow, Plate 603/2, page 66, over most of the surface; basal area is near Empire Yellow, Plate 603, page 66; inside surface: Aureolin, Plate 3/1, page 3, near the base, fading rapidly upward to become near Empire Yellow, Plate 603/2, page 66, in the upper portions.

*General color effect.*—Newly opened flower—between Aureolin, Plate 3/1, page 3, and Lemon Yellow, Plate 4/2, page 4. Three days open—near Empire Yellow, Plate 603/2, page 66.

*Behavior.*—Drop off cleanly except for occasional petaloids; fading to between Empire Yellow, Plate 603/3, page 66, and Primrose Yellow, Plate 601/3, page 65.

*Flower longevity.*—On bush in garden—3 to 5 days in September. Cut roses grown outdoors kept at living-room temperatures—3 to 4 days in September.

*Reproductive organs*

Stamens: Average number, about 50; arranged regularly about pistils; a few mixed with petaloids.

Filaments: Medium length; 10 to 15 mm. long; most with anthers. Color—Aureolin, Plate 3, page 3.

Anthers: Medium size, 3 to 6 mm. long; all open at once approximately. Color—central portion: Canary Yellow, Plate 2/2, page 2; Edges: :Indian Yellow, Plate 6, page 6.

Pollen: Moderate. Color—near Buttercup Yellow, Plate 5/1, page 5.

Pistils: Average number; approximately 69 in number.

Styles: Moderately uneven; short to average length; thin; loosely bunched. Color—Upper ⅓: near Nopal Red, Plate I (Ridgway); lower portions: near Primrose Yellow, Plate 601/2, page 65.

Stigma: Color—near Aureolin, Plate 3/1, page 3.

Ovaries: All enclosed in calyx.

Hips: Globular; moderately smooth, glaucous; walls thick, fleshy. Color—¾ mature near Chrysolite Green, Plate XXXI (Ridgway).

Sepals: Permanent; medium length to long; spear-shaped; recurved. Color (from newly opened flower)—inside: near Light Grape Green, Plate XLI (Ridgway), covered with whitish tomentum; outside: near Courge Green, Plate XVII (Ridgway).

Seeds: Average number; usually medium size; 8 to 20 in number.

*Plant*

Foliage:

Leaves.—Compound of usually 5 leaflets; normal to abundant; large; moderately heavy to somewhat leathery, non-glossy and flat.

*Leaflets.*—Shape—ovoid with apex subacute; base round; margin doubly serrate.

*Color.*—Mature—upper surface: near Grass Green, Plate VI (Ridgway); under surface: between Courge Green, Plate XVII, Ridgway), and Light Grape Green, Plate XLI (Ridgway). Young—upper surface: near Biscay Green, Plate XVII (Ridgway). The edges of the serrations and the midrib often overlaid with Mineral Red, Plate XXVII (Ridgway); Under surface: Base color near Light Grape Green, Plate XLI (Ridgway), overlaid with varying amounts of Hydrangea Red, Plate XXVII (Ridgway).

*Rachis.*—Average size to heavy. Upper side—grooved with some stipitate glands an edges. Under side—moderately smooth, usually with a few prickles and with a few stipitate glands.

*Stipules.*—Medium length to long; medium width, with medium length points, turning out at an angle of more than 45°, recurved toward the stem.

*Disease.*—More than average resistant to mildew.

Growth:

*Habit.*—Upright; moderately branched.

*Growth.*—Very vigorous.

*Canes.*—Heavy.

*Main stems.*—Color—near Deep Chrysolite Green, Plate XXXI (Ridgway). *Large prickles*—medium length to long, about 1 cm.; hooked slightly downward; with moderately long broad base. Color—between Brick Red, Plate XIII (Ridgway), and Russet, Plate XV (Ridgway). *Small prickles*—none. *Hairs*—none.

*Branches.*—Color—near Absinthe Green, Plate XXXI (Ridgway). *Large prickles*—several; medium length, about 7 mm.; hooked downward; with medium length, moderately narrow base. Color—near Chrysolite Green, Plate XXXI (Ridgway), overlaid with varying amounts of Hydrangea Red, Plate XXVII (Ridgway). *Small prickles*—none. *Hairs*—none.

*New shoots.*—Color—base color is near Calliste Green, Plate VI (Ridgway), heavily overlaid with Corinthian Red, Plate XXVII (Ridgway). *Large prickles*—several; medium length, about 6 mm.; hooked downward; with medium length, moderately narrow base. Color—near Clear Dull Green Yellow, Plate XVII (Ridgway), overlaid in basal region with Corinthian Red, Plate XXVII (Ridgway). *Small prickles*—none. *Hairs*—none.

I claim:

A new and distinct variety of rose plant of the hybrid tea class, characterized as to novelty by the very vigorous and upright habits of growth of the plant, by the abundance of large, relatively flat, dark green foliage, by the brilliant yellow color and the persistence thereof in the buds and open flowers throughout their entire life, and by the notable absence of any other color shadings in the flowers, substantially as herein shown and described.

HERBERT C. SWIM.

No references cited.